United States Patent [19]
Hoetzel

[11] Patent Number: 5,389,223
[45] Date of Patent: Feb. 14, 1995

[54] ELECTROCHEMICAL MEASURING SENSOR

[75] Inventor: Gerhard Hoetzel, Stuttgart, Germany

[73] Assignee: Robert Bosch GmbH, Stuttgart, Germany

[21] Appl. No.: 62,497

[22] Filed: May 17, 1993

Related U.S. Application Data

[63] Continuation of Ser. No. 635,615, Jan. 4, 1991, abandoned.

[30] Foreign Application Priority Data

Jul. 23, 1988 [DE] Germany ............... 3825139

[51] Int. Cl.⁶ ......................................... G01N 27/419
[52] U.S. Cl. ............................ 204/425; 204/426; 204/427; 204/428
[58] Field of Search ...................... 204/421–429, 204/153.18

[56] References Cited

U.S. PATENT DOCUMENTS

| | | | |
|---|---|---|---|
| 3,342,716 | 9/1967 | Anderson et al. | 204/196 |
| 3,475,227 | 10/1969 | Caule et al. | 148/6.31 |
| 3,907,657 | 9/1975 | Heijne et al. | 204/427 |
| 4,172,247 | 10/1979 | Ikeura | 204/427 |
| 4,310,401 | 1/1982 | Stahl et al. | 204/426 |
| 4,430,192 | 2/1984 | Maeda | 204/427 |
| 4,502,939 | 3/1985 | Holfelder et al. | 204/429 |
| 4,505,807 | 3/1985 | Yamada | 204/425 |
| 4,568,443 | 2/1986 | Asayama et al. | 204/410 |
| 4,610,741 | 9/1986 | Mase et al. | 156/89 |
| 4,617,795 | 10/1986 | Abthoff et al. | 204/424 |
| 4,647,364 | 3/1987 | Mase et al. | 204/426 |
| 4,683,049 | 7/1987 | Nakajima et al. | 204/428 |
| 4,728,411 | 3/1988 | Mase et al. | 204/426 |
| 4,875,990 | 10/1989 | Kodachi | 204/427 |

FOREIGN PATENT DOCUMENTS

| | | |
|---|---|---|
| 3606044 | 9/1986 | Germany . |
| 2187842 | 9/1989 | United Kingdom . |

*Primary Examiner*—T. Tung
*Attorney, Agent, or Firm*—Frishauf, Holtz, Goodman & Woodward

[57] ABSTRACT

An electrochemical measuring sensor for the determination of the air/fuel ratio in exhaust gases of internal combustion engines both in the low-fuel and also in the fuel-rich range with a sensor element with an electrochemical oxygen concentration cell and an oxygen pumping cell with solid electrolyte base is proposed, in which the sensor element is arranged in a housing, capable of insertion in the exhaust gas pipe, in a manner such that the electrodes of the electrochemical oxygen concentration cell and of the oxygen pumping cell of the sensor element in the measuring sensor are situated outside the exhaust gas pipe, the communication with the atmosphere taking place via openings in the housing and the communication with the exhaust gas taking place via a diffusion slit. The sensor element is characterized by a particularly simple construction, free oxygen being available to the oxygen pumping cell both in the lean and also in the rich lambda range. The electrodes of the oxygen pumping cell can be of large dimension, for which reason only comparatively small current densities are necessary. A severe cooling of the sensor element in the electrode range due to cold exhaust gas (test gas) is prevented.

16 Claims, 4 Drawing Sheets

EXHAUST GAS

EXHAUST GAS →

ELECTROCHEMICAL MEASURING SENSOR

This application is a continuation of application Ser. No. 07/635,615, filed Jan. 4, 1991, now abandoned.

PRIOR ART

The invention is based on an electrochemical measuring sensor.

Electrochemical measuring sensors for the determination of the oxygen content of gases, in particular of exhaust gases of internal combustion engines, having a metallic housing in whose longitudinal bore an essentially platelet-like sensor element is firmly and hermetically built-in in the longitudinal direction that one of its ends is situated in the region of the opening, on the test-gas side, of the housing, the sensor element being exposed to the test gas by means of at least one of its two porous laminar electrodes arranged at a distance from one another on a solid electrolyte which conducts oxygen ions are known from German Offenlegungsschrift 2,937,048 and German Offenlegungsschrift 3,017,947.

Characteristic of these electrochemical measuring sensors, which are also designated lambda probes, is that their built-in sensor element is composed of an electrochemical oxygen concentration cell (Nernst cell) which, when displaced in two chambers, is exposed either to the exhaust gas or to the air. They are unsuitable for the determination of the air/fuel ratio in exhaust gases of internal combustion engines both in the low-fuel and also in the fuel-rich region.

Furthermore, electrochemical measuring sensors which, in addition to an electrochemical oxygen concentration cell, also comprise an oxygen pumping cell and as a consequence thereof, are capable of determining or measuring the air/fuel ratio of an air/fuel mixture over the entire operating range of the combustion unit, including the lean range up to an enrichment range are known from U.S. Pat. No. 4,568,443 ASAYAMA et al./MITSUBISHI+NGK, and German Patent Specification 3,606,044 HAYAKAWA et al.

A disadvantage of the lastmentioned electrochemical measuring sensors is that they always require 2 air reference chambers and their construction is comparatively complicated and expensive.

ADVANTAGES OF THE INVENTION

The electrochemical measuring sensor according to the invention having the features of the main claim has, on the other hand, important advantages. Thus, the sensor element of the measuring sensor has a particularly simple construction, i.e. its manufacture requires, in the simplest case, only 2 solid-electrolyte sheets or ceramic sheets. Free oxygen is available for the oxygen pumping cell both in the lean and also in the rich lambda range, i.e. an $H_2O$ or $CO_2$ decomposition to produce $O_2$ ions is not necessary in the rich range. The electrodes of the oxygen pumping cell can be of large dimension in the longitudinal direction, for which reason only comparatively small current densities are necessary. Furthermore, severe cooling of the sensor element due to cold test gas does not occur in the region of the electrodes since the electrodes are situated outside the exhaust gas pipe through which flow takes place and communicate with the exhaust gas to be tested only via the gas diffusion slit, after the fashion of an extremely short "bypass".

DRAWING

The drawing serves to explain the invention in more detail.

In detail,

DETAILED DESCRIPTION

Figure 1:
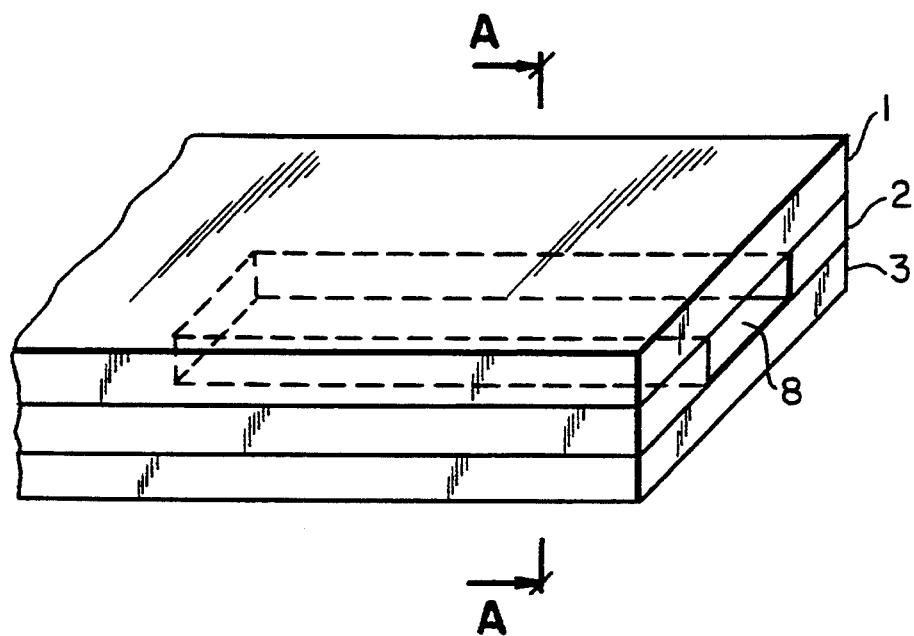
FIG. 1 shows the construction of a sensor element of an electrochemical measuring sensor according to the invention.
Figure 2:
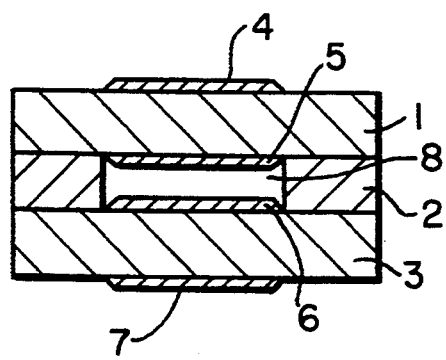
FIG. 2 shows the sensor element of FIG. 1 in section along the section line A—A.

FIGS. 1 and 2 illustrate the construction of an advantageous embodiment of a sensor element of an electrochemical measuring sensor according to the invention. The sensor element is composed of the solid electrolyte sheets 1, 2 and 3, the electrodes 4 and 5 of the oxygen pumping cell (pumping electrodes) and the electrodes 6 and 7 of the electrochemical oxygen concentration cell (sensor electrodes).

The solid electrolyte sheet 2 has a punched-out diffusion channel 8. For better clarity, the electrodes have not been included in the drawing in FIG. 1. According to the layout shown in FIG. 3 of a first advantageous embodiment of a sensor element of an electrochemical measuring sensor according to the invention, the sensor element is manufactured by laminating the solid electrolyte sheets 1, 2 and 3 together. Before laminating the sheets together, the through-contact hole is punched out of the sheet 1. Furthermore, the external pumping electrode 4 together with conductor track 10 and contact 11, and also the internal pumping electrode 5 together with conductor track 10' and contact 11' are printed on the sheet 1. In a corresponding manner, the through-contact hole 9' is punched out of the sheet 3. Furthermore, the internal sensor electrode 6 together with conductor track 10" and contact 11", and also the external sensor electrode 7 together with conductor track 10''', and contact 11''', are printed on the sheet 3. In the case of this first embodiment, the heater has been omitted since the position of the same is not critical.

Figure 3:
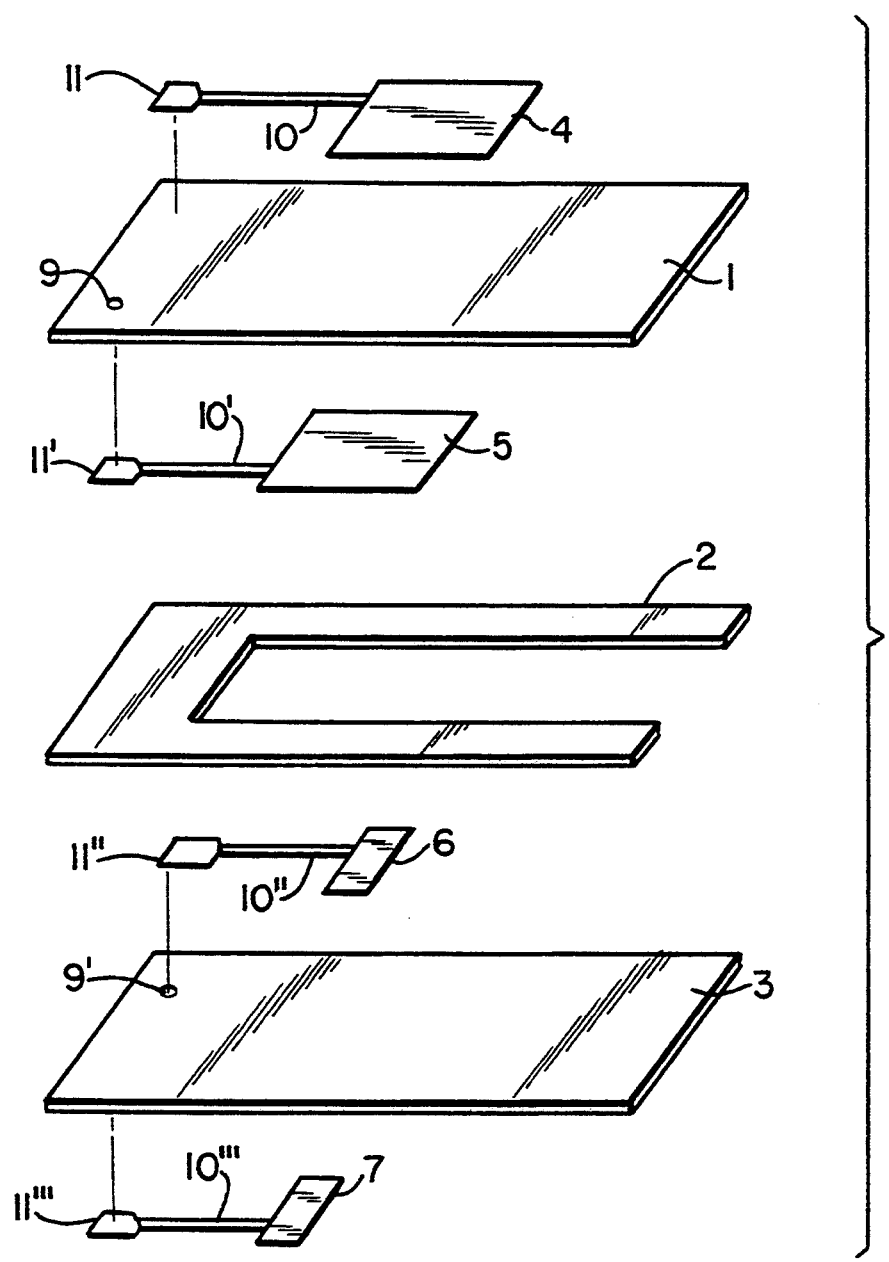
FIG. 3 shows the layout of a first embodiment of a sensor element of an electrochemical measuring sensor according to the invention without integrated heater.
Figure 4:
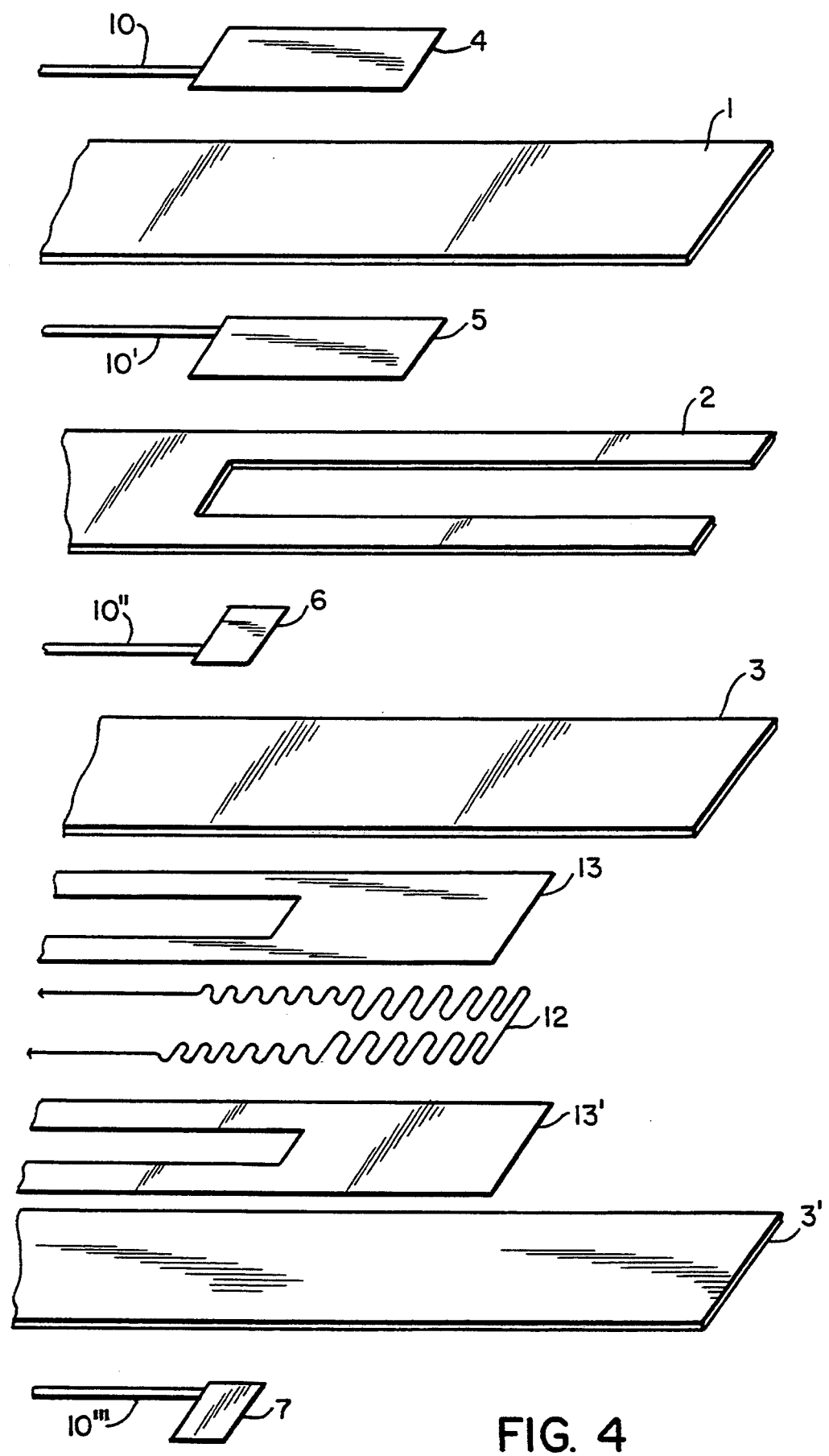
FIG. 4 shows the layout of a second embodiment of a sensor element of an electrochemical measuring sensor according to the invention with integrated heater.

The second embodiment, shown in FIG. 4, of a sensor element of an electrochemical measuring sensor according to the invention differs from the embodiment shown in FIG. 3 essentially by the provision of a heater 12 which, in the case of the embodiment shown, is installed between the sheets 3 and 3' and is insulated from the sheets 3 and 3' by the insulations 13, 13'. In the case of this advantageous development of a sensor element of a measuring sensor according to the invention, the sensor element is consequently produced by laminating the sheets 1, 2, 3 and 3' together, the insulations 13, 13' and the heater 12 being furthermore also printed onto the sheets 3 and 3' in addition to the electrodes, conductor tracks and contacts.

Figure 5:
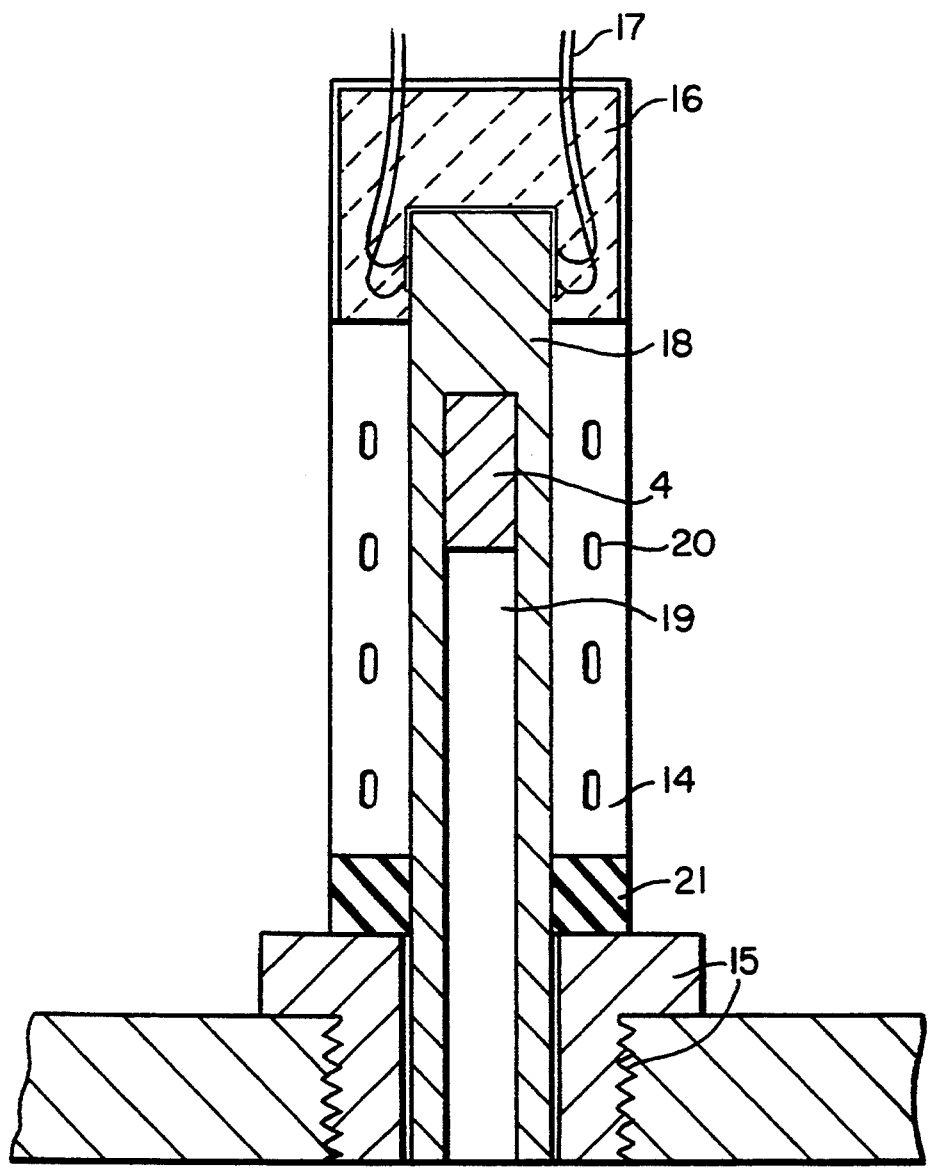
FIG. 5 shows an electrochemical measuring sensor according to the invention in section.

The embodiment, shown by way of example in FIG. 5, of an electrochemical measuring sensor 18 according to the invention is essentially composed of a metallic housing 14 whose one end has a hexagonal wreck-engagement surface and a thread 15 for screwing into the exhaust gas channel and whose other end has a ceramic plug 16 with contact springs 17. Fitted into the longitudinal bore of the housing is the sensor element with the electrodes 4–7. The access of test gas to the electrodes takes place via the gas diffusion slit 19 and the access of air via the air inlet openings 20. The seal 21 seals the reference air chamber from the exhaust gas chamber. Housing construction and arrangement of the sensor element in the housing are, however, not critical.

Known solid electrolyte sheets which conduct $O_{2-}$–ions and are based on oxides of tetravalent metals such as, in particular, $ZrO_2$, $CeO_2$, $HfO_2$ and $ThO_2$ with a content of divalent alkaline earth oxides and/or preferably trivalent oxides of the rare earths are suitable for producing the sensor elements of the electrochemical measuring sensors according to the invention. In a typical manner, the sheets may be composed of up to about 50 to 97 mole-% of $ZrO_2$, $CeO_2$, $HfO_2$ or $ThO_2$ and of up to 50 to 3 mole-% of CaO, MgO or SrO and/or oxides of the rare earths and in particular of $Y_2O_3$. In an advantageous manner, the solid electrolyte sheets are composed of $ZrO_2$ stabilized with $Y_2O_3$. In an expedient manner, the thickness of the sheets used is 0.1 to 0.6 mm.

The electrodes, the associated conductor tracks and contacts may be printed on the solid electrolyte sheets, optionally partially provided with an insulating layer, in a conventional known manner starting from known pastes with a noble-metal base, in particular platinum cermet base.

In an advantageous manner, the electrodes of the oxygen pumping cell of the sensor element are formed with a larger area than the electrodes of the oxygen concentration cell. This means that, in an advantageous manner, the area of the electrodes of the oxygen pumping cell can be 10 to 500% larger than the area of the electrodes of the oxygen concentration cell.

The heater conductor tracks can be insulated from the solid electrolyte sheets, for example, by means of conventionally known insulations, for example, with an $Al_2O_3$ base.

The through-contacting of the solid electrolyte sheets can also be carried out by conventional known methods.

In the case of the advantageous embodiments, shown in the drawings, of sensor elements of electrochemical measuring sensors according to the invention, the diffusion channel is formed by using a solid electrolyte sheet out of which the diffusion channel is punched. The use of such a sheet is, however, not necessary. On the contrary, it is also possible to produce the diffusion channel in another manner. Thus, according to a further advantageous development of the invention, to construct the sensor element it is also possible to use only two solid electrolyte sheets which are printed beforehand with a combustible, decomposable or volatilized substance such as, for example, theobromine, indanthrene blue, soot or the like in the region forming the diffusion channel. In this case, the diffusion channel is produced by heating the sheet laminate to a temperature necessary for the combustion, decomposition or volatilization of the substance used. In an advantageous manner, this process stage may follow the laminating together of the sheets or be combined with the laminating-together.

Such substances, as also the electrodes, conductor tracks and electrode contacts may be printed on by conventional known methods, for example by the screen-printing process.

The solid electrolyte sheets of the sensor elements of the electrochemical measuring sensors according to the invention are also laminated together by conventional known methods using conventional known interlaminar binders.

I claim:

1. An apparatus comprising
an electrochemical measuring sensor for determination of the air/fuel ratio in exhaust gas from an internal combustion engine, both in a fuel-lean range and in a fuel-rich range, having
a sensor element with
a housing (14) having a first end secured by a screw-in connection to a sidewall of an exhaust pipe of said internal combustion engine, and a second end remote from said exhaust pipe, said housing defining a reference gas chamber and a test gas chamber therewithin;
a seal (21), located adjacent said first housing end, separating from each other said reference gas and test gas chambers;
an electrochemical oxygen concentration cell and
an oxygen pumping cell, each with a solid electrolyte base, which are situated in said housing (14), facing each other, to define a diffusion slit intermediate space which serves as said test gas chamber (19), said intermediate space communicating with the exhaust gas in said exhaust pipe,
wherein
each of said cells includes a pair of electrodes; and
in order to remove said pairs of electrodes from thermal influence by cold exhaust gas,
the electrodes (4, 5) of the oxygen pumping cell and the electrodes (6, 7) of the electrochemical oxygen concentration cell of the sensor element in the measuring sensor are situated in a portion of the housing (14) remote from said screw-in connection and outside the exhaust pipe, a first one (4) of the electrodes of the oxygen pumping cell and a first one (7) of the electrodes of the electrochemical oxygen concentration cell being directly exposed to the ambient atmosphere via openings (20) into said reference gas chamber in the housing (14).

2. An apparatus with an electrochemical measuring sensor according to claim 1,
wherein
the oxygen concentration cell and the oxygen pumping cell of the sensor element are each composed of a solid electrolyte sheet (1, 3) with electrodes printed on both sides by thick-film technology.

3. An apparatus with an electrochemical measuring sensor according to claim 2,
wherein
the two solid electrolyte sheets (1, 3) are separated from one another by a further solid electrolyte sheet (2) with punched-out diffusion slit (8).

4. An apparatus with an electrochemical measuring sensor according to claim 3,
wherein
the sensor element has a heater (12) insulated from the solid electrolyte sheets.

5. An apparatus with an electrochemical measuring sensor according to claim 3,
wherein
the housing (14) has a hexagonal wrench-engagement surface and with an external thread (15).

6. An apparatus with an electrochemical measuring sensor according to claim 3, wherein
electrical supply of the sensor element takes place via a ceramic plug (16) with contact springs (17).

7. An apparatus with an electrochemical measuring sensor according to claim 2,
wherein
the sensor element has a heater (12) insulated from the solid electrolyte sheets.

8. An apparatus with an electrochemical measuring sensor according to claim 2,
wherein
the housing (14) has a hexagonal wrench-engagement surface and an external thread (15).

9. An apparatus with an electrochemical measuring sensor according to claim 2,
wherein
electrical supply of the sensor element takes place via a ceramic plug (16) with contact springs (17).

10. An apparatus with an electrochemical measuring sensor according to claim 1,
wherein
the electrodes (4, 5) of the oxygen pumping cell are formed with a larger area than the electrodes (6, 7) of the oxygen concentration cell.

11. An apparatus with an electrochemical measuring sensor according to claim 10,
wherein
the sensor element has a heater (12) insulated from the solid electrolyte bases.

12. An apparatus with an electrochemical measuring sensor according to claim 10,
wherein
the housing (14) has a hexagonal wrench-engagement surface and an external thread (15).

13. An apparatus with an electrochemical measuring sensor according to claim 10,
wherein
electrical supply of the sensor element takes place via a ceramic plug (16) with contact springs (17).

14. An apparatus with an electrochemical measuring sensor according to claim 1,
wherein
the sensor element has a heater (12) insulated from the solid electrolyte bases.

15. An apparatus with an electrochemical measuring sensor according to claim 1,
wherein
the housing (14) has a hexagonal wrench-engagement surface and an external thread (15).

16. An apparatus with an electrochemical measuring sensor according to claim 1,
wherein
electrical supply to the sensor element takes place via a ceramic plug (16) with contact springs (17).

* * * * *